United States Patent [19]

Kaiser et al.

[11] Patent Number: 4,731,412
[45] Date of Patent: Mar. 15, 1988

[54] PROCESS AND COMPOSITION FOR AMINO-TERMINAL, α-ASPARTYL AND α-GLUTAMYL DIPEPTIDE ESTERS

[75] Inventors: Emil T. Kaiser, New York, N.Y.; Gary F. Musso, San Diego, Calif.

[73] Assignee: The Salk Institute Biotechnology/Industrial Associates, Inc., San Diego, Calif.

[21] Appl. No.: 851,444

[22] Filed: Apr. 14, 1986

Related U.S. Application Data

[62] Division of Ser. No. 687,475, Dec. 28, 1984, Pat. No. 4,600,532.

[51] Int. Cl.$^4$ .............................................. C08F 8/32
[52] U.S. Cl. .............................. 525/54.11; 525/328.2; 530/334
[58] Field of Search .................. 525/54.11, 328.2; 530/334

[56] References Cited

U.S. PATENT DOCUMENTS

| 3,462,460 | 8/1969  | Kollonitsch    | 260/345.9   |
| 3,786,039 | 1/1974  | Ariyoshi et al.| 260/112.5   |
| 3,798,206 | 3/1974  | Uchiyama et al.| 260/112.5   |
| 3,833,553 | 9/1974  | Ariyoshi et al.| 260/112.5   |
| 3,920,626 | 11/1975 | Ariyoshi et al.| 260/112.5   |
| 3,962,207 | 6/1976  | Uchiyama et al.| 260/112.5 R |
| 3,985,715 | 10/1976 | Gray           | 525/54.11   |
| 4,089,821 | 5/1978  | Enkoji et al.  | 525/54.11   |
| 4,171,412 | 10/1979 | Coupek et al.  | 525/54.11   |
| 4,242,238 | 12/1980 | Colescott et al.| 525/54.11  |
| 4,301,045 | 11/1981 | Kaiser et al.  | 525/54.11   |
| 4,426,324 | 1/1984  | Meienhofer     | 260/112.5 R |
| 4,507,230 | 3/1985  | Tom et al.     | 525/54.11   |

OTHER PUBLICATIONS

Fujino and Nishimura, "The Use of Simple Ketoximes in Peptide Synthesis," Chem. Pharm. Bull. (Japan) 17, 1937–1941 (1969).
Ariyoshi et al., "The Synthesis of a Sweet Peptide . . . Without the Use of Protecting Groups," Bull. Chem. Soc. (Japan) 46, 1893–1895 (1973).
Ariyoshi et al., "The Synthesis of Salts of L. Aspartic Anhydride with Alkyl-Sulfuric Acid and Their Use in the Preparation of Aspartylphenylalanie Methyl Ester," Bull. Chem. Soc. (Japan) 46, 2611–2612 (1973).
DeGrado and Kaiser, "Polymer-Bound Oxime Esters As Supports for Solid-Phase Peptide Synthesis, Preparation of Protected Peptide Fragments," J. Org. Chem. 45, 1295–1300 (1980).
Vinick and Jung, "A Superior Synthesis of Aspartame," Tetrahedro Lett. 23, 1315–1318 (1982).
DeGrado and Kaiser, "Solid-Phase Synthesis of Protected Peptides on a Polymer-Bound Oxime . . . ," J. Org. Chem. 47, 3258–3261 (1982).
Nakagawa and Kaiser, "Synthesis of Protected Peptide Segments and Their Assembly on a Polymer-Bound Oxime," J. Org. Chem. 48, 678–685 (1983).
Hayashi and Shimizu, "Reactivity of Aromatic o-Hydroxy Oximes II," Bull. Chem. Soc. (Japan) 56, 3197–3198 (1983).

Primary Examiner—Edward J. Smith
Assistant Examiner—Bernard Lipman
Attorney, Agent, or Firm—Fitch, Even, Tabin & Flannery

[57] ABSTRACT

Reaction of a ketoxime-derivatized resin with a strong acid salt of aspartic anhydride or glutamic anhydride yields a novel aspartyl or glutamyl ketoxime ester-derivatized resin, wherein the aspartyl or glutamyl groups are esterified predominantly at the α-carboxyl group and wherein the aspartyl or glutamyl groups are not covalently protected at the amino group or the carboxyl group that is not esterified. Aminolysis in the presence of a weak acid of the novel aspartyl or glutamyl ketoxime ester-derivatized resin, wherein the aspartyl or glutamyl groups remain as the strong acid salt, with a salt of an amino acid with a base or an amino acid ester yields the corresponding dipeptide or dipeptide ester. After aminoylsis, the ketoxime-derivatized resin can be reused. An advantageous solid-phase method is thus provided for making α-L-aspartyl dipeptide ester sweeteners, including aspartame, and the immunopotentiating dipeptide, α-L-glutamyl-L-asparagine.

6 Claims, No Drawings

PROCESS AND COMPOSITION FOR AMINO-TERMINAL, α-ASPARTYL AND α-GLUTAMYL DIPEPTIDE ESTERS

This is a division of application Ser. No. 687,475, filed Dec. 28, 1984, now U.S. Pat. No. 4,600,532.

TECHNICAL FIELD

The present invention concerns processes and compositions for making amino-terminal, α-aspartyl and α-glutamyl dipeptides and dipeptide esters. More particularly, the invention relates to solid phase processes for making such peptides and peptide esters and to derivatized polymer resin intermediates in such processes.

BACKGROUND OF THE INVENTION

A number of α-L-aspartyl, dipeptide esters are known to be intensely sweet and useful as sweeteners. R. Mazur et al., J. Am. Chem. Soc. 91, 2684–2691 (1969); U.S. Pat. Nos. 3,920,626; 3,492,131 and 3,475,403. Among these, aspartame (α-L-aspartyl-L-phenylalanine methyl ester) is now being used extensively in the food and beverage industries.

α-L-glutamyl-L-asparagine, and pharmaceutically acceptable salts thereof, are known to be therapeutically useful as immunopotentiating agents in humans and other mammals. U.S. Pat. No. 4,426,324.

A number of methods of making aspartame and the other α-L-aspartyl, dipeptide ester sweeteners are also known. See, for example, the references cited above in connection with dipeptide ester sweeteners, as well as Vinick and Jung, Tetrahedron Lett. 23, 1315–1318 (1982), and U.S. Pat. Nos. 3,962,207; 3,833,553; 3,798,206 and 3,786,039.

Several methods for making aspartame and other lower alkyl esters of α-L-aspartyl phenylalanine have been disclosed wherein a strong acid salt of L-aspartic anhydride is reacted with the methyl, or other lower alkyl, ester of L-phenylalanine or an acid solution thereof, see U.S. Pats. Nos. 3,962,207; 3,833,553; 3,798,206 and 3,786,039. A problem encountered in such syntheses is that the reactivity of the β-carboxyl of the aspartic anhydride with the amino group of the phenylalanine ester is approximately one quarter to the same as that of the α-carboxyl, unless the reaction is run under conditions which enhance the reactivity of the α-carboxyl relative to that of the β-carboxyl. The product resulting from condensation of the β-carboxyl, β-L-aspartyl phenylalanine methyl ester, is bitter and, therefore, an undesirable contaminant in aspartame preparations. It has been found that reacting strong acid salts of L-aspartic anhydride with L-phenylalanine lower alkyl esters in the presence of weak acids reduces the reactivity of the β-carboxyl of the aspartic anhydride, relative to that of the α-carboxyl, by as much as 50% and, further, increases the total yield of both of the dipeptide esters, see U.S. Pat. No. 3,833,553.

The use of oxime and ketoxime esters of covalently protected amino acids in peptide synthesis is known. See, e.g., Hayashi and Shimizu, Bull. Chem. Soc. Japan 56, 3197–3198 (1983); Fujino and Nishimura, Chem. Pharm. Bull. 17, 1937 (1969). Aminolysis of oxime and ketoxime esters of covalently protected amino acids with amino acid esters, and catalysis of such aminolysis with weak acids, such as acetic acid or formic acid, are known. See, e.g., Hayashi and Shimizu, supra.

The use in solid-phase peptide synthesis of amino acid ketoxime ester-derivatized polystyrene resins has been reported, wherein the polymer-supported amino acid residues have protecting groups covalently bound to their amino groups and the corresponding ketoxime is formed with a phenyl group of the polystyrene support and a phenyl group, or substituted phenyl group selected from p-nitro, p-chloro and p-methoxy phenyl, provided by acylation of the polystyrene phenyl group with a benzoyl, or p-substituted benzoyl, halide. DeGrado and Kaiser, J. Org. Chem. 45, 1295-1300 (1980); DeGrado and Kaiser, J. Org. Chem. 47, 3258-3261 (1982); Nakagawa and Kaiser, J. Org. Chem. 48, 678-685 (1983). Aminolysis with amino acid esters of the polymer-supported, p-nitrobenzophenone ketoxime esters of covalently protected amino acids and peptides, and catalysis of such aminolysis with acetic acid, have also been reported. DeGrado and Kaiser, 1980 and 1982, supra; Nakagawa and Kaiser, 1983, supra.

Ketoxime esters of aspartic acid and glutamic acid, without protecting groups covalently bound to the amino group or unesterified carboxyl group, have not been known heretofore.

SUMMARY OF THE INVENTION

It has now been discovered that a strong acid salt of aspartic or glutamic anhydride, without a covalently bound protecting group, reacts with ketoxime-derivatized polymer resins to form the corresponding novel, polymer-supported ketoxime ester.

Further, it has been found that aminolysis in the presence of weak acid of the polymer-supported ketoxime ester, wherein the aspartyl or glutamyl group remains as the strong acid salt, with an amino acid ester or a salt of an amino acid with a base yields the corresponding dipeptide ester or dipeptide, respectively, and ketoxime-derivatized resin. The ketoxime-derivatized resin can be reused.

The aspartic or glutamic anhydride strong acid salt reacts with the ketoxime-derivatized resin predominantly through the α-carboxyl of the aspartyl or glutamyl group.

Further, in the aminolysis reaction, in the presence of weak acid, the amino acid ester or salt of an amino acid with a base will react, with negligible racemization, predominantly at the polymer-bound carboxyl of the polymer-supported aspartyl or glutamyl group.

Thus, an advantageous, solid-phase method for synthesizing L-α-aspartyl, dipeptide ester sweeteners, especially aspartame, and L-α-glutomyl dipeptides, such as L-α-glutamyl-L-asparagine, has been found. Among its advantages, the method involves no costly protection and deprotection of amino or carboxyl groups.

The dipeptides and dipeptide esters made by the method of the invention are useful per se or useful as intermediates in making polypeptides or polypeptide esters which include the dipeptides or dipeptide esters in their sequences.

DETAILED DESCRIPTION OF THE INVENTION

A process has been discovered for making a dipeptide or dipeptide ester, or a salt thereof, with an N-terminal α-aspartyl or α-glutamyl which comprises reacting a strong acid salt of aspartic anhydride or glutamic anhydride, respectively, with a ketoxima-derivatized polymer and reacting, in the presence of weak acid, the resulting novel aspartyl or glutamyl ketoxime ester-derivatized polymer, wherein the aspartyl or glutamyl groups remaing as the strong acid salt, with a salt with a base, or an ester, of the carboxy-terminal amino acid corresponding to the dipeptide or dipeptide ester, respectively.

The invention thus entails a process for making a compound of formula I, or a salt thereof,

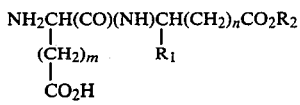

wherein m is 1 or 2;

wherein, when m is 2, n is 0, $R_1$ is —$CH_2C(O)NH_2$, and $R_2$ is hydrogen;

wherein, when m is 1, n is 0, 1 or 2;

wherein, when m is 1 and n is 0, $R_1$ is benzyl, p-hydroxybenzyl, p-methoxybenzyl, p-ethoxybenzyl, methylthiomethyl, methylthioethyl, methylsulfonylethyl, or —$CH_2O(CO)R_3$, wherein $R_3$ is methyl, ethyl, n-propyl or i-propyl;

wherein, when n is 1 or 2, $R_1$ is hydrogen or methyl;

wherein, if $R_1$ is benzyl, p-hydroxybenzyl or methylthioethyl, $R_2$ is methyl, ethyl, n-propyl, i-propyl or t-butyl;

wherein, if $R_1$ is hydrogen or methyl, $R_2$ is methyl, ethyl, n-propyl or i-propyl;

wherein, if $R_1$ is p-methoxybenzyl, p-ethoxybenzyl, methylthiomethyl, methylsulfonylethyl or —$CH_2O(CO)R_3$, $R_2$ is methyl or ethyl;

wherein the configuration of the amino-terminal aspartyl or glutamyl group is L; and wherein the configuration at the carbon to which $R_1$ is bonded is L, if n is 0, and D, if n is 1 or 2 and $R_1$ is methyl, which comprises:

(i) reacting a strong acid salt of a compound of formula II

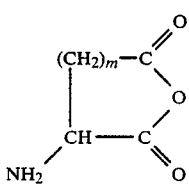

wherein m is as in the compound of formula I and the configuration at the asymmetric carbon is L or D,L, with a ketoxime-derivatized polymer; and (ii) reacting, in the presence of weak acid, the novel aspartyl or glutamyl ketoxime ester-derivatized polymer from step (i), wherein the aspartyl or glutamyl group remains as a strong acid salt, with a compound of formula III

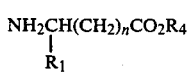

wherein n and $R_1$ are as in the compound of formula I; wherein, if $R_2$ in the compound of formula I is not hydrogen, $R_4$ is the same as $R_2$; wherein, if $R_2$ in the compound of formula I is hydrogen, $R_4$ is a cation corresponding to a base of which the compound of formula III is a salt; and wherein the configuration at the asymmetric carbon is L or D,L, if n is 0, and D or D,L, if n is 1 or 2 and $R_1$ is methyl.

Use herein of the term "ketoxime" indicates an oxime formed by reaction of hydroxylamine with a ketone.

Use herein of the terms "D,L" as a prefix to the name of a compound, or a designation of configuration at an asymmetric carbon in a compound, unless otherwise indicated, indicates a mixture of the enantiomorphs of the compound wherein each enantiomorph is a substantial fraction (i.e., at least about 1%) of the mixture.

The compounds of formula I are known. Those wherein m is 1 are useful as sweetners of foods and beverages. That wherein m is 2 is useful therapeutically as an immunopotentiating agent in mammals, including humans (U.S. Pat. No. 4,426,324).

The preferred applications of the invention are to making the compounds of formula I wherein m is 1, n is 0, $R_1$ is benzyl, p-hydroxybenzyl or methylthioethyl, and $R_2$ is methyl, i.e. α-L-aspartyl-L-phenylalanine methyl ester (also known as aspartame), α-L-aspartyl-L-tyrosine methyl ester, and α-L-aspartyl-L-methionine methyl ester. The most preferred application is to making aspartame.

Strong acid salts of L- and D,L-aspartic anhydride and L- and D,L-glutamic anhydride (compounds of formula II) are also known and include those of strong mineral acids, such a hydrochloric, hydrobromic, hydroiodic, sulfuric, chlorosulfonic, bromosulfonic, perchloric and nitric acids; those formed with monoesters of sulfuric acid, such a methylsulfuric, ethylsulfuric, isopropylsulfuric and benzylsulfuric acids; those formed with organic sulfonic acids, such as benzenesulphonic, p-toluenesulfonic, β-naphthalenesulfonic, and alkylsufonic acids such as methylsulfonic, ethylsulfonic and isopropylsulfonic acid; and those formed with halogenated carboxylic acids, such as trichloroacetic, dichloroacetic and trifluoroacetic acids. See U.S. Pat. Nos. 3,462,460 and 3,816,471; and Ariyoshi et al. Bull. Chem. Soc. (Japan) 45, 2208 (1972) and 46, 2611 (1973). The glutamic anhydride salts are prepared in essentially the same way as the aspartic anhydride salts, beginning with glutamic acid rather than aspartic acid. Preferred for use in the present invention are the hydrochloric and methylsulfuric acid salts of aspartic and glutamic anhydride.

The compounds of formula III, wherein $R_4$ is the same as $R_2$ in the corresponding compound of formula I, are known, both as essentially pure D or L isomer and as mixtures of both isomers.

$R_4$ in the compound of formula III, when $R_2$ in the corresponding compound of formula I is hydrogen, can be any cation, corresponding to a base of which the compound of formula III is a salt. The bases used to make the salts of formula III are, generally, bases which are strong enough to maintain the amino group on a substantial fraction of the amino acid in the free amine form yet not so strong or nucleophilic as to cause significant racemization of the amino acid. Such bases include sodium or potassium bicarbonate, N-alkylmorpholines (e.g., N-methylomorpholine, N-ethylmorpholine), piperidine, and trialkylamines. Preferred are trialkylamines wherein the alkyl moieties are the same or different and are each of 1 to 3 carbon atoms. Compounds of formula III which are salts of amino acids with such bases are known, or readily synthesized by the skilled, both as essentially pure D or L isomer and as mixtures of both isomers.

Weak acids which can be employed in the aminolysis reaction (reaction step (ii), supra) with the compound of formula III include, generally, acids which, in aqueous solution at 25° C., have dissociation constants less than $3 \times 10^{-M}$ and preferably less than $10^{-4}M$. If an acid has more than one ionizable hydrogen atom, the dissociation constant for the first such hydrogen atom will be less than $3 \times 10^{-2}M$, and preferably less than $10^{-4}M$, in aqueous solution at 25° C. Such weak acids include phosphoric acid, phosphorous acid, carbonic acid, formic acid, alkylcarboxylic acids such as acetic, proprionic and n-butyric acids, monohalogenated alkylcarboxylic acids such as chloroacetic, bromoacetic and iodoacetic acids, citric acid, succinic acid and phenol. Preferred is acetic acid.

Preferably the amount of weak acid present in the aminolysis reaction mixture is equimolar with the total amount of compound of formula III initially present in the reaction mixture. By "total amount of compound of formula III" is meant the amount of such compound in both of its forms: with the amino group protonated and as free amine. If $R_2$ in the corresponding compound of formula I is hydrogen, the "total amount of compound of formula III" includes also the analogs of the compound, in both protonated amine and free amine forms, wherein the carboxyl group is in anionic form, protonated form, and associated with cations, other than $R_4$ and protons, that might be present.

Optionally, the addition salt, with the weak acid, of the compound of formula III can be used to provide both weak acid and compound of formula III to the aminolysis reaction mixture.

Ketoxime-derivatized polymers employed in the present invention include those described by DeGrado and Kaiser, 1980 and 1982, supra.

Any polymer which can be ketone-derivatized can be employed to make the ketoxime-derivatized polymers utilized in the invention. Preferred is polystyrene, optionally crosslinked by copolymerization with suitable crosslinking compounds.

Most preferred for the present invention are polystyrene resins optionally crosslinked by co-polymerization with 0.5% to 3%, by weight, divinylbenzene. Preferably, the resin will be used in the form of small, spherical beads of about 100 to about 1000 mesh in size.

An example of resin beads that can be used to make ketoxime-derivatized polymer for use in the invention is Biobeads SX1 TM, a polystyrene-1% divinylbenzene resin provided in the form of spherical beads, 200–400 mesh in size, by Bio-Rad Laboratories, Inc., Richmond, Calif., U.S.A.

To form the ketoxime-derivatized polymer for use in the invention, a polymer is typically first acylated at a repeating group to form the ketone-derivatized polymer and the ketone-derivatized polymer is then reacted with hydroxylamine to form the corresponding ketoxime-derivatized polymer.

Ketozime-derivatized polymers for use in the invention include those wherein the ketoxime-derivatized sites are represented by formula IV

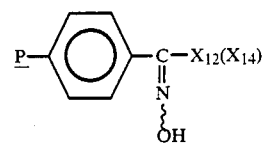

wherein P represents the polymer backbone; the phenylene group between P and C=N—OH is a repeating group in the polymer and is present in the (polystyrene) polymer prior to formation of the ketoxime derivative; wherein $X_{12}$ is (i) phenyl optionally substituted at any one position with chlorine; bromine; iodine; alkoxy, wherein the alkyl moiety is of 1 to 6 carbon atoms; sulfonyl; nitro; or trialkylamino, wherein the alkyl groups are the same or different and are each of 1 to 4 carbon atoms; (ii) alkyl of 1 to 6 carbon atoms, optionally substituted at any one position with nitro, hydrogensulfate, sulfonyl, or trialkylamino, wherein the alkyl groups are the same or different and are each of 1 to 4 carbon atoms; (iii) cycloalkyl of 3 to 8 carbon atoms, optionally substituted at any one position with nitro, hydrogensulfate, sulfonyl, or trialkylamino, wherein the alkyl groups are the same or different and are each of 1 to 4 carbon atoms; or (iv) a heterocyclic moiety consisting of 3 or 4 $CH_2$ groups in the ring; an atom or group selected from oxygen, nitrogen, sulfur and sulfonyl in the ring; and a CH group in the ring and bonded to the ketoxime carbon atom; and wherein $X_{14}$ is a counterion to any charge that is present on $X_{12}$ and is the conjugate base of a strong acid. $X_{14}$ will typically be a univalent anion corresponding to a strong acid, e.g., chloride or methylsulfate.

Preferred among the polymers of formula IV are those wherein $X_{12}$ is phenyl or phenyl substituted in the para-position with methoxy, chlorine, bromine, nitro or (trimethyl)amino.

The preparation of ketoxime-derivatized polymers of formula IV is known in the art. See DeGrado and Kaiser, 1980 and 1982, supra.

The process of the invention can also be carried out with a ketoxime-derivatized polymer wherein the ketoxime-derivatized sites are represented by formula V

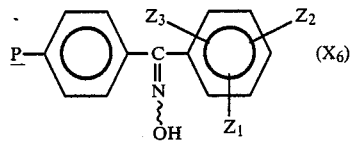

wherein P represents the polymer backbone; wherein the phenylene group between P and C=N—OH is a repeating group in the polymer and is present in the polymer prior to formation of the ketoxime derivative; wherein $Z_1$, $Z_2$ and $Z_3$ are at any three positions on the phenyl group and are the same or different, each being selected from hydrogen; chlorine; bromine; iodine; alkoxy, alkylsulfonyl, and alkylsulfonic, wherein the alkyl group is of 1 to 6 carbon atoms; trialkylamino, wherein the alkyl groups are the same or different and are each of 1 to 4 carbon atoms; nitro; and sulfonyl; provided that not more than one of $Z_1$, $Z_2$ and $Z_3$ is hydrogen; and wherein $X_6$ represents the counterion or counterions to any charge that is present on the substituted phenyl group and consists of one or more conjugate bases of strong acids. $X_6$ will typically be one or more univalent anions corresponding to strong acids, e.g. chloride, methylsulfate. Preferred among the polymers of formula V is that wherein the substituted phenyl group is o-methoxy-p-(trimethylamino)phenyl.

The ketoxime-derivatized polymers according to formulas IV and V are made in essentially the same way. First, the ketone-derivatized polymer is made by Friedel-Crafts acylation of the repeating phenyl groups of the polymer with a compound of formula VI or VII

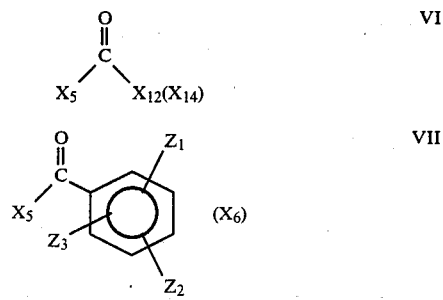

corresponding to the derivative to be added to the polymer. In formulas VI and VII, $X_5$ is chlorine or bromine, preferably chlorine; $X_{12}$ and $X_{14}$ are as defined above for the compound of formula IV; and $Z_1$, $Z_2$, $Z_3$ and $X_6$ are as defined above for the compound of formula V. Compounds of formulas VI and VII are readily available or readily made by the skilled person.

The acylation of the resin is carried out in the presence of a Lewis acid catalyst, preferably $AlCl_3$, in an anhydrous, aprotic solvent such as ethyl acetate, dimethylformamide, an aromatic or nitrated aromatic hydrocarbon (e.g. benzene, toluene, nitrobenzene), a halogenated hydrocarbon (e.g. 1,2-dicloroethane), a polyether (e.g. polyethylene glycol), or a mixture of any of the foregoing.

As the skilled will recognize, the choice of solvent will be indicated primarily by the reactivity of the acylating compound. With the more reactive compounds, the reaction will be run at a temperature near or below room temperature (e.g. 0° C. to 30° C.); and any of the solvents or mixtures of solvents which remain sufficiently fluid at the reaction temperature to permit efficient stirring can be used. With less reactive acylating compounds, the reaction will need to be carried out at higher temperatures (e.g. 30° C. to 100° C.) to proceed reasonably rapidly; in these cases, a solvent or mixture of solvents which refluxes at a suitable temperature is preferably used. The refluxing reaction mixture will additionally be efficiently stirred.

Swelling of the resin that occurs with some of the solvents for the acylation reaction is also desirable.

The acylation reaction is carried out over about 4 to about 36 hours, preferably 8 to 24 hours, with a molar amount of acylating agent that is typically 5% to 50% of that of phenyl groups in the resin to be acylated.

The extent of acylation of the polymer will depend on a number of factors, including the reactivity of the acylating agent, the accessibility of phenyl groups in the resin to acylating agent (which in turn will depend on the extent of swelling of the polymer, the concentration of acylating agent in the reaction mixture, and the efficiency with which the stirring of the reaction mixture permits acylating agent to diffuse into the polymer particles), and the temperature and duration of the acylation reaction.

Compounds of formula VII, wherein one or more of $Z_1$, $Z_2$ and $Z_3$ would be reactive in the Friedel-Crafts acylation reaction mixture, must be suitably protected at these reactive groups prior to the acylation reaction and then deprotected after the acylation reaction.

The ketone-derivatized polymer is recovered by filtration and thoroughly washed with suitable solvents to remove unreacted reagents. A suitable washing protocol is provided in Example I.

Typically 5% to 30% of the phenyl groups of the polystyrene resin are acylated by the above procedure. The extent of acylation can be determined by a number of techniques known in the art, including measuring weight-gain by the resin.

The ketoxime-derivatized polymer is then prepared as follows from the washed, ketone-derivatized polymer:

The washed, ketone-derivatized polymer is added slowly, with efficient stirring, to a solution of a strong acid salt of hydroxylamine, approximately equimolar in base (e.g., pyridine), in a polar, non-aqueous solvent such as a lower alkanol or cyclic ether. The solution is efficiently stirred and maintained at 20° C.–120° C. for about 4 to 48 hours. The preferred strong acid salt of the hydroxylamine is the hydrochloride, the preferred base is pyridine, the preferred solvent is ethanol, the preferred reaction temperature is 80° C., and the preferred reaction time is 8–12 hours. Hydroxylamine is present in 5–50 fold molar excess, preferably 15–25 fold molar excess, with respect to ketone groups on the ketone-derivatized polymer.

"Efficient stirring" in the present specification means stirring or shaking that maintains the surface of resin particles in contact with solution, so that reagent can readily diffuse into the particles to reach sites for reaction, but that is not so vigorous that it causes fragmentation of the resin particles.

Ketoxime-derivatized polymer is recovered from the reaction mixture by filtration and is then thoroughly washed with suitable solvents to remove unreacted reagents and reaction by-products. A suitable washing procedure is provided in the fourth paragraph of Example I.

After the washing, the resin is dried in vacuo.

The extent of conversion of ketone-carbonyl groups to ketoxime groups by the above procedure is 90%–100%.

As indicated by the wavy line representing the bond between the ketoxime hydroxyl, or ketoxime ester linked aspartyl or glutamyl group, and ketoxime nitrogen in various figures in the present specification representing ketoxime-derivatized or ketoxime ester-derivatized polymers, such polymers utilized in the present invention have a combination of syn and anti configurations about the ketoxime C=N double bond.

Novel, aspartyl or glutamyl ketoxime ester-derivatized polymer is then formed from the ketoxime-derivatized polymer as follows:

To an efficiently stirred mixture of ketoxime-derivatized polymer in a polar, aprotic solvent, such as halogenated hydrocarbons, (e.g., methylene chloride, chloroform), nitroalkanes (e.g., nitromethane), acetonitrile, cyclic ethers (e.g. tetrahydrofuran), dimethylformamide, ethylacetate, or a mixture of any of them, is added a strong acid salt of L- or D,L-aspartic anhydride or L- or D,L-glutamic anhydride. The amount of anhydride salt added preferably approximately equals the amount required stoichiometrically for complete esterification of ketoxime groups in the resin.

After addition of the anhydride salt, the reaction is continued at a temperature, between about −50° C. to about 40° C., at which efficient stirring can be maintained, for from about 10 minutes to about 10 hours. Preferred solvents for the reaction are those which do not appreciably shrink the ketoxime-derivatized resin and wherein the strong acid salt of glutamic or aspartic anhydride is sufficiently soluble for the derivativization reaction to proceed at a reasonably rapid rate. Non-aqueous, protic solvents (e.g. methanol) may be used but tend to destabilize the anhydrides. Generally, a solvent such as 50% (v/v) acetonitrile in tetrahydrofuran or 50% (v/v) ethylacetate in either acetonitrile or nitromethane will be acceptable. The preferred temperature of the reaction is room temperature, i.e. approximately 20° C. to approximately 30° C. Typically, more than half of the ketoxime nitrogens in the resin will be converted to ketoxime ester nitrogens in the foregoing procedure.

After completion of the reaction, the aspartyl or glutamyl ketoxime ester-derivatized polymer (resin) is separated by filtration and, preferably, thoroughly washed with a non-aqueous, polar, preferably aprotic, solvent suitable to remove unreacted anhydride acid salt and reaction by-products. Nitromethane, acetonitrile, tetrahydrofuran, ethylacetate, dimethylformamide or mixtures of them are suitable for this purpose.

The washing step after formation of the glutamyl or aspartyl ketoxime ester-derivatized polymer is not necessary to obtain dipeptide or dipeptide ester product in accordance with the novel process described herein. However, said washing step, by eliminating from the resin unreacted acid salt of aspartic or glutamic anhydride and various other impurities, substantially increases the yield of desired dipeptide or dipeptide ester product from the final step in the process, to be described below.

The synthesis, and optional post-synthesis washing, of ketoxine ester-derivatized resin are preferably carried out so that the aspartyl or glutamyl residues on the resin remain as the strong acid salts.

As will be apparent to those of skill, if anions represented by $X_{14}$ (Formula IV) or $X_6$ (Formula V) are present in the ketoxime-derivatized polymer, those anions and that corresponding to the strong acid of the strong acid salt of the aspartyl or glutamyl group will intermix in the aspartyl or glutamyl ketoxime ester-derivatized resin. Thus, a fraction of the aspartyl or glutamyl groups in such resins will be associated with $X_{14}$ or $X_6$. $X_{14}$, or $X_6$, may be the same as, or different from, the anion corresponding to the strong acid of the strong acid salt of aspartic or glutamic anhydride used to make the aspartyl or glutamyl ketoxime ester-derivatized resin.

In addition to the fact that the aspartyl and glutamyl ketoxime ester-derivatized resin, when made as described above with a strong acid salt of aspartic or glutamic anhydride, respectively, has no protecting groups covalently bound to the aspartic acid or glutamic acid amino groups or unesterified carboxyl groups, a preponderance of the amino acid residues in the ketoxime ester-derivatized resin so formed are esterified through the α-carboxyl group.

Preparation of the compound of formula I from a compound of formula III and aspartyl or glutamyl ketoxime ester-derivatized polymer proceeds via aminolysis of the ketoxime ester as follows:

A solution is prepared of a compound of Formula III, in a polar, non-aqueous solvent such as methanol, ethanol, tetrahydrofuran, acetonitrile, nitromethane, ethylacetate, dimethylformamide, or a mixture of any of them.

To prepare the solution, the compound of Formula III itself can be dissolved to the desired concentration in the desired solvent. Alternatively, an acid addition salt (e.g. hydrochloride) of compound of Formula III can be used to prepare the solution.

It is essential that a substantial fraction of the compound of formula III in this solution have the amino group in the free amine form. Thus, if an acid addition salt (e.g. hydrochloride) of a compound of formula III is used to prepare the solution, at least a portion of the acid of the acid addition salt must be neutralized. The base used in such neutralization is strong enough so that, at the concentration employed, a substantial fraction of the compound of formula III will be in the free amine form but not so strong or nucleophilic as to cause significant racemization of the amino acid or amino acid ester. Such bases include sodium or potassium bicarbonate, N-alkylmorpholines (e.g. N-methylmorpholine, N-ethylmorpholine), piperidine, and trialkylamines. Preferred are trialkylamines wherein the alkyl groups are the same or different and are each of 1 to 3 carbon atoms. Preferably, the acid addition salt will be neutralized with an equimolar amount of base in preparing the solution of compound of Formula III.

In preparing a solution of a compound of Formula III, which corresponds to a compound of Formula I wherein $R_2$ is hydrogen, from an acide addition salt of the amino acid corresponding to the compound of formula III, preferably the same base will be used to prepare the compound of Formula III from the amino acid and neutralize the acid (e.g. hydrochloride) corresponding to the acid addition salt. If the corresponding amino acid is used to prepare the compound of Formula III, preferably the amount of base used will be equimolar with the amount of amino acid. If an acid addition salt of the amino acid is used to prepare the compound of Formula III, preferably the amount of base used will be twice the molar amount of the acid addition salt.

As indicated, preparation of a solution of a compound of Formula III can involve concomitant production of salts, other than compounds of Formula III, such as, e.g., trialkylammonium chlorides. By numerous methods well known in the art, (e.g. chromatographic, solvent extraction), these salts can optionally be separated from the compounds of Formula III before a solution of the compound of Formula III for use in the aminolysis reaction is finally prepared. If these salts are not separated from the compound of Formula III prior to aminolysis, they will be mixed with the compound of Formula I and salts thereof formed in the aminolysis.

The aminolysis is conducted in the presence of weak acid. Thus, in the preferred procedure, after the solution of compound of Formula III is prepared, it is mixed with an aliquot of weak acid and then used in aminolysis. The weak acid is preferably added directly to the solution of compound of Formula III. It can, however, be added in solution in a suitable polar, non-aqueous solvent (e.g. methanol, ethanol tetrahydrofuran, acetonitrile, nitromethane, ethylacetate, dimethylformamide, or a mixture of any of them).

The amount of weak acid in the aminolysis reaction mixture is preferably equimolar with the total amount of compound of Formula III initially present in the reaction mixture. Thus, an addition salt of the weak acid with a compound of Formula III may be used directly in preparing a solution to be used in aminolysis, rather than first preparing a solution of compound of formula III and then adding weak acid to that solution.

In yet another alternative procedure, rather than adding weak acid to the solution of compound of Formula III to prepare a solution for the aminolysis, the weak acid can be added instead to the solvent in which aspartyl or glutamyl ketoxime ester-derivatized resin is suspended for the aminolysis, prior to addition of solution of compounds of Formula III to the resin suspension.

For the aminolysis, the solution of compound of Formula III, preferably including an amount of weak acid equimolar with the total amount of compound of Formula III, is added to an efficiently stirred suspension of aspartyl or glutamyl ketoxime ester-derivatized resin, wherein the aspartyl or glutamyl groups remain as strong acid salt, in a polar, non-aqueous solvent such as methanol, ethanol, tetrahydrofuran, acetonitrile, nitromethane, ethylacetate, dimethylformamide, or a mixture of any of them. The solvent is preferably the same as that of the solution, of the compound of Formula III (preferably together with weak acid), added to the resin suspension for the aminolysis reaction.

The reaction mixture is stirred at 0° C. to 60° C., preferably at room temperature (20° C.-30° C.), for about 2 to 24 hours, preferably about 4 to about 8 hours. The reaction can be run essentially to completion.

The total amount of compound of Formula III initially present in the aminolysis reaction mixture is 0.5 to 5 times, preferably 1 to 1.5 times, the number of moles of the aspartyl or glutamyl groups bound in the resin.

After completion of the aminolysis, resin is separated from solvent by filtration and washed with polar, non-aqueous solvents suitable to remove reactants and reaction products from the resin. The washing procedures in the final paragraph of Example I or in Examples IV or V are suitable. Further, a suitable composition for the solvent used for washing is the composition of the solvent in which the compound of Formula III is dissolved for mixing with the suspension of ester-derivatized resin for the aminolysis reaction.

The washed resin is then recharged with strong acid salt of aspartic anhydride or glutamic anhydride, as described above for formation of the aspartyl or glutamyl ketoxime ester-derivatized polymer, including optionally washing after the derivativization. The recharged resin is then reused in an aminolysis reaction to make a compound of formula I.

It is found that a preponderance of the compound of formula III that reacts, in the presence of weak acid, with the aspartyl or glutamyl groups in the ketoxime ester-derivatized resin, wherein the aspartyl or glutamyl groups are present as strong acid salt, reacts at the $\alpha$-carboxyl of the aspartyl or glutamyl groups to form acid addition salt(s) of the compound of formula I, if $R_2$ in said compound is not hydrogen, or acid addition salt(s) of compounds formed by replacing $R_2$ in the compound of formula I, if $R_2$ is hydrogen, with $R_4$ (and other cations that might be present). The anion of the acid addition salt(s) will include the anion corresponding to the strong acid associated with the aspartyl or glutamyl groups and $X_{14}$ (FIG. IV) or $X_6$ (FIG. V). If $X_{14}$ (or $X_6$) differs from the anion of the strong acid salt of the aspartyl or glutamyl groups, there will be different acid addition salts formed, one corresponding to said anion and another to $X_{14}$ (or $X_6$).

The filtrate obtained upon separation of resin from the aminolysis reaction mixture will include the weak acid, essentially completely undissociated; the acid addition salt(s), described in the previous paragraph, of the compound of formula I, if $R_4$ is not hydrogen; or, if $R_2$ is hydrogen, of salt(s) of the compound of formula I with hydrogen replaced by $R_4$ and other cations that might be present; and salts of bases, if base was used in preparing the solution of the compound of Formula III used in aminolysis and salts (other than of compound of Formula III) formed by said base were not separated from the solution prior to its use in aminolysis; possibly unreacted compound of Formula III (as a salt or salts); and various other compounds (impurities).

The compound of Formula I, or a salt thereof, can be prepared from this filtrate, or from salts prepared from the filtrate, by methods, including acid-and base-neutralization, solvent extraction, recrystallization and chromatographic methods, well known in the art. See, e.g. U.S. Pat. Nos. 4,426,324; 3,920,626; 3,833,553 and 3,798,206; and Ariyoshi et al., Bull. Chem. Soc. (Japan) 46, 1898 (1973). The compound of Formula I, or a salt thereof, may be obtained in anhydrous or hydrated form.

The preferred salts of the compounds of formula I are those acceptable for human consumption, for the compounds intended for use in foods and beverages, or acceptable for administration to humans by injection, for the compounds intended for therapeutic use. The preferred salts include those formed with physiologically acceptable cations, such as sodium, potassium, calcium, magnesium or ammonium, as well as acid addition salts, of the compound of formula I or a salt thereof prepared with one or more physiologically acceptable cations, that are formed with physiologically acceptable acids, such as acetic, hydrobromic, hydrochloric, and sulfuric.

If optically impure aspartic or glutamic anhydride or optically impure compound of formula III is used in making compound of Formula I by the process of the present invention, the product from aminolysis will be a mixture of stereoisomers, usually only one of which will be active (as a sweetener or immunopotentiating agent). The presence of inactive isomers with the active one will lessen, but not eliminate, the activity (i.e. sweetness or pharmacological activity) of the final product. Thus, resolution of the various isomers will not be necessary in many applications. If resolution of the isomers to isolate the active one is desired, persons of skill in the art are aware of numerous methods for resolving them.

Persons of skill will also recognize how dipeptides and dipeptide esters, that can be made by the methods of the present invention, can be used as intermediates in the synthesis of polypeptides or polypeptide esters which include in their sequences the dipeptides and dipeptide esters provided by the present invention.

The present invention is illustrated further in the following examples:

EXAMPLE I

Benzophenone Ketoxime-derivatized Resin

Benzophenone ketoxime-derivatized polymer (resin) is prepared following essentially the procedure outlined in DeGrado and Kaiser, J. Org. Chem. 47, 3258–3261 (1982).

1% divinylbenzene-polystyrene copolymer resin, in the form of beads with a 200–400 mesh diameter and sold as Biobeads SX1, is obtained from Bio-Rad Laboratories, Inc., Richmond, Calif., U.S.A.

9 g of benzoyl chloride and 12 g of $AlCl_3$ are dissolved in 100 ml of nitrobenzene that has been dried over 3A molecular sieves. The resulting solution is filtered into a dropping funnel.

70.0 g of the Biobeads SX1 resin beads is added to 1200 ml of 1,2-dichloroethane, that has been distilled from phosphorous pentoxide immediately prior to use; and to this mixture, which has been brought to vigorous reflux and is stirred efficiently (to maintain surface of resin beads in contact with solvent and promote efficient transfer of reagents into the resin) in added dropwise, over a period of 30 minutes, the above-described solution of benzoyl chloride and $AlCl_3$ in 100 ml of nitrobenzene. Stirring and refluxing of the resulting mixture is continued for 12 hours; the resin is then filtered and washed as follows: 3 times, each with 1 liter of 3 parts dioxane to 1 part 4N HCl; 3 times, each with 1 liter of 3 parts dioxane to 1 part $H_2O$; 3 times, each with 1 liter of dimethylformamide; and 3 times, each with 500 ml of methanol. Finally, the resin is dried in vacuo.

The resulting ketone polymer is added over a 30 minute period to an efficiently stirred, boiling solution of 70 g hydroxylamine hydrochloride, 100 ml pyridine and 500 ml ethanol. Efficient stirring during addition of ketone polymer to the solution is essential for quantitative conversion of ketone to oxime. The resulting mixture is stirred under reflux for 8 hrs. after all ketone polymer has been added. Finally, the resin is collected by filtration and washed as follows: 3 times, each with 500 ml of 3 parts methanol in 1 part water; 2 times, each with 500 ml of dimethylformamide; and 3 times, each with 300 ml of methanol.

EXAMPLE II p-Nitrobenzophenone Ketoxime-derivatized Resin p-Nitrobenzophenone ketoxime-derivatized polymer (resin) was prepared in the same way as the resin of Example I, except that 12 g of p-nitrobenzoyl chloride was used in place of 9 g of benzoylchloride as a starting material. As determined by weight-gain of the resin, in the resulting ketone-derivatized polymer there were 0.59 mmol of p-nitrobenzoyl added per gram of ketone-derivatized polymer. In the formation of ketoxime-drivatized polymer, essentially complete conversion of ketone to ketoxime occurred.

EXAMPLE III

Phenyl, Methyl Ketoxime-derivatized Resin

To prepare the title resin, the procedure of Example I is used except that 5 g of acetyl chloride is used in place of 9 g of benzoyl chloride as starting material.

EXAMPLE IV

Preparation of Aspartyl Ketoxime Ester-derivatized Resin and α-L-Aspartyl-L-Phenylalanine Methyl Ester 13.0 g of p-nitrobenzophenone ketoxime-derivatized resin, that was prepared substantially according to Example II and contained approximately 10 mmole of ketoxime groups, was mixed with 150 ml of a mixture of 2 parts (v/v) ethylacetate, 2 parts (v/v) acetonitrile and 1 part (v/v) methanol (referred to hereafter in this Example as "2:2:1 solvent"). To this resin mixture was added, with efficient stirring, 2.4 g (10 mmole) of the methylsulfuric acid salt of L-aspartic anhydride. The stirring was continued for 6 hours at room temperature (approx. 25° C.), whereupon the derivativization of resin with aspartyl groups appeared to be complete, as no aspartic anhydride salt was evident upon thin-layer chromatographic analysis of solvent.

The resulting aspartyl ketoxime ester-derivatized resin was washed 3 times, each time with 75 ml of the 2:2:1 solvent.

2.1 g (10 mmole) of L-phenylalanine methyl ester hydrochloride was dissolved in 75 ml of the 2:2:1 solvent. To this solution was first added 1.37 ml (10 mmole) triethylamine and, after 1–2 minutes of mixing, 0.6 ml (10 mmole) of acetic acid. The resulting solution was then added slowly to an efficiently stirred solution of the above-prepared aspartyl ketoxime ester-derivatized resin (comprising approximately 10 mmole of aspartyl hydrogenmethylsulfate groups) in 75 ml of the 2:2:1 solvent. The reaction was continued with efficient stirring at room temperature (approx. 25° C.) for 24 hours. After 24 hours, resin was separated from solvent by filtration.

The filtrate was analyzed for products by high performance liquid chromatography (HPLC). Several products were observed. Dipeptide ester products eluted from the HPLC column as the perchloric acid salt. One product eluted in the same fraction as the perchloric acid salt of genuine aspartame had in a control run. One product, which eluted slightly more slowly than, and was present at about half the amount of, the aspartame salt, was identified as the corresponding salt of β-L-aspartyl-L-phenylalanine methylester.

EXAMPLE V

Preparation of Glutamyl Ketoxime Ester-derivatized Resin and α-L-Glutamyl-L-Asparagine 17 g of benzophenone ketoxime-derivatized resin according to Example I (and containing approximately 10 mmole of ketoxime groups) is mixed with 150 ml of 1 part (v/v) tetrahydrofuran and 1 part (v/v) acetonitrile (referred to hereafter as "1:1 solvent"). To this resin mixture is added, with efficient stirring, 1.7 g (10 mmole) of L-glutamic anhydride hydrochloride. The stirring is continued for 6 hours at room temperature (25° C.).

The resulting glutamyl ketoxime ester-derivatized resin is washed as follows: 3 times, each with 75 ml of 1:1 solvent; 3 times, each with 50 ml of acetonitrile; and, finally, 2 times, each 75 ml of 1:1 solvent.

2.0 g (12 mmole) of L-asparagine hydrochloride is dissolved in 1000 ml of 1:1 solvent at room temperature. To this solution, maintained at room temperature, is added, with efficient stirring, 3.5 ml (20 mmole) of diisopropylethylamine (DIEA).

The washed glutamyl ketoxime ester-derivatized resin, comprising approximately 10 mmole of glutamyl hydrochloride groups, is mixed with 200 ml of 1:1 solvent and to the mixture is added 0.6 ml (10 mmole) of acetic acid. The mixture is then stirred efficiently while the above-described solution of L-asparagine hydrochloride with DIEA is added to it. The reaction is continued at room temperature with efficient stirring for 24 hours. After 48 hours, the resin is separated from solvent by filtration.

The filtrate includes the diisopropylethylammonium salt of α-L-glutamyl-L-asparagine hydrochloride.

The foregoing example illustrate the present invention, but are not intended to limit the scope of the invention. Those skilled in the art will recognize modifications and variations of the exemplified embodiments that are within the spirit and scope of the invention described and claimed in the present specification.

What is claimed is:

1. A ketoxime ester-derivatized resin wherein the ester-derivatized sites are represented by formula X

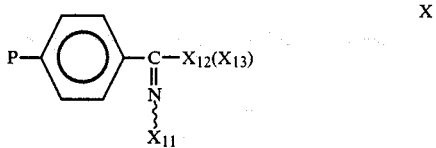

wherein P represents the polymer backbone of the resin; wherein the phenylene group is a repeating functional group in the corresponding underivatized polymer; wherein $X_{11}$ is a strong acid salt of L- or D,L-aspartyl or a strong acid salt of L- or D,L-glutamyl, which is bonded to the ketoxime-nitrogen through the α or β carboxyl group, and is not covalently protected at either the amino group or the carboxyl group that is not bonded to the ketoxime-nitrogen, provided that the fraction of $X_{11}$ groups in the resin bonded to the ketoxime-nitrogen through the α-carboxyl and with a configuration of L is greater than 0; wherein $X_{12}$ is (i) phenyl, or phenyl substituted at any one position with chlorine; bromine; iodine; alkoxy, wherein the alkyl moiety is of 1 to 6 carbon atoms; sulfonyl; nitro; or trialkylamino, wherein the alkyl groups are the same or different and are each of 1 to 4 carbon; (iii) cycloakyl of 3 to 8 carbon atoms; or (iv) a heterocyclic moiety consisting of 3 or 4 carbon atoms in the ring, an atom or group selected from oxygen, nitrogen, sulfur and sulfonyl in the ring, and a CH group in the ring and bonded to the ketoxime carbon atom; and wherein $X_{13}$ is a counterion to any positive charge that is present on $X_{12}$ and is the conjugate base of a strong acid.

2. A ketoxime ester-derivatized resin according to claim 1 wherein P is polystyrene optionally cross-linked with 0.5% to 3%, by weight, divinylbenzene; $X_{11}$ is a strong acid salt of L-aspartyl or a strong acid salt of L-glutamyl; and $X_{12}$ is methyl, phenyl, p-nitrophenyl, p-chlorophenyl, p-bromophenyl, p-methoxyphenyl, or p-(trimethylamino)phenyl; provided that, if $X_{12}$ is (trimethylamino)phenyl, at least a portion of the counterions represented by $X_{13}$ is chloride or bromide.

3. A ketoxime ester-derivatized resin according to claim 2 wherein $X_{11}$ is L-aspartyl chloride, bromide, iodide, methylsulfate, ethylsulfate, isopropylsulfate, benzylsulfate, methylsulfonate, ethylsulfonate, benzenesulfonate, p-toluenesulfonate, β-naphthalensulfonate, chlorosulfonate, bromosulfonate, nitrate, perchlorate, trichloroacetate, trifluoroacetate or dichloroacetate; provided that, if $X_{12}$ is (trimethylamino)phenyl, at least a portion of the $X_{11}$ groups is L-aspartyl hydrochloride or L-aspartyl hydrobromide.

4. A ketoxime ester-derivatized resin according to claim 2 wherein $X_{11}$ is L-glutamyl chloride, bromide, iodide, methylsulfate, ethylsulfate, isopropylsulfate, benzylsulfate, methylsulfonate, ethylsulfonate, benzenesulfonate, p-toluenesulfonate, β-naphthalensulfonate, chlorosulfonate, bromosulfonate; nitrate; perchlorate; trichloroacetate, trifluosoacetate or dichloroacetate; provided that, if $X_{12}$ is (trimethylamino)phenyl, at least a portion of the $X_{11}$ groups is L-glutamyl hydrochloride or L-glutamyl hydrobromide.

5. A ketoxime ester-derivatized resin according to claim 3 wherein $X_{12}$ is phenyl or p-nitrophenyl and $X_{11}$ is L-aspartyl hydrochloride or L-aspartyl hydrogenmethylsulfate.

6. A ketoxime ester-derivatized polymer according to claim 4 wherein $X_{12}$ is phenyl or p-nitrophenyl and $X_{11}$ is L-glutamyl hydrochloride or L-glutamyl hydrogenmethylsulfate.

* * * * *

UNITED STATES PATENT AND TRADEMARK OFFICE
CERTIFICATE OF CORRECTION

PATENT NO. : 4,731,412            Page 1 of 2
DATED : March 15, 1988
INVENTOR(S) : Emil Thomas Kaiser, et al.

It is certified that error appears in the above-identified patent and that said Letters Patent is hereby corrected as shown below:

On the Title Page:

In Line 3 of the Title, after "α-GLUTAMYL" add --DIPEPTIDES AND--.

In Line 13 of U.S. Patent Documents cited, change "Tom" to --Tam--.

In Line 16 of Other Publications, change "Tetrahedro" to --Tetrahedron--.

| | |
|---|---|
| Column 1, Line 4: | After "α-GLUTAMYL" add --DIPEPTIDES AND--. |
| Column 2, Line 66: | Change "ketoxima" to --ketoxime--. |
| Column 3, Line 2: | Change "remaing" to --remain--. |
| Column 5, Line 5: | Change "$3 \times 10^- M$" to --$3 \times 10^{-2} M$--. |
| Column 5, Line 42: | Change "ketozime" to --ketoxime--. |
| Column 5, Line 66: | Change "ketozime" to --ketoxime--. |
| Column 6, Line 9: | Change "P" to --$\underline{P}$--. |
| Column 6, Line 10: | Change "P" to --$\underline{P}$--. |
| Column 6, Line 10: | Change "C=N-OH" to --C=N~OH--. |
| Column 6, Line 55: | Change "P" to --$\underline{P}$--. |
| Column 6, Line 56: | Change "P" to --$\underline{P}$--. |

UNITED STATES PATENT AND TRADEMARK OFFICE
CERTIFICATE OF CORRECTION

PATENT NO.   : 4,731,412                              Page 2 of 2
DATED        : March 15, 1988
INVENTOR(S)  : Emil Thomas Kaiser, et al.

It is certified that error appears in the above-identified patent and that said Letters Patent is hereby corrected as shown below:

Column 6, Line 56:      Change "C=N-OH" to --C=N~OH--.

Column 9, Line 44:      Change "ketoxine" to --ketoxime--.

Column 10, Line 37:     Change "acide" to --acid--.

Column 13, Line 24:     Change "in" to --is--.

Column 14, Line 63:     After "each" add --with--.

Column 15, Line 13:     Change "example" to --examples--.

Column 15, Line 25:     Change "P" to --$\underline{P}$--.

Column 15, Line 30:     Change "P" to --$\underline{P}$--.

Column 15, Line 46:     After "carbon" add --atoms; (ii) alkyl of 1 to 6 carbon atoms--.

Column 16, Line 9:      Change "P" to --$\underline{P}$--.

Signed and Sealed this

Eleventh Day of October, 1988

Attest:

DONALD J. QUIGG

Attesting Officer    Commissioner of Patents and Trademarks